United States Patent [19]

Reeves

[11] Patent Number: 4,594,466
[45] Date of Patent: Jun. 10, 1986

[54] RECOVERY OF ALCOHOLS

[75] Inventor: Russell R. Reeves, Richmond, Australia

[73] Assignee: Apace Research Limited, Richmond, Australia

[21] Appl. No.: 761,482

[22] Filed: Aug. 1, 1985

[30] Foreign Application Priority Data

Aug. 22, 1984 [AU] Australia .............................. PG6711

[51] Int. Cl.$^4$ ...................... C07C 29/74; C07C 31/08
[52] U.S. Cl. .................................. 568/919; 435/161; 568/916
[58] Field of Search ................. 568/919, 916; 435/161

[56] References Cited

U.S. PATENT DOCUMENTS

| | | | |
|---|---|---|---|
| 1,350,254 | 8/1920 | Frankforter | 568/916 |
| 3,501,535 | 3/1970 | Stringer et al. | 260/632.5 |
| 4,277,635 | 7/1981 | Oulman et al. | 568/917 |
| 4,321,328 | 3/1982 | Hoge | 435/161 |
| 4,454,359 | 6/1984 | Colgrove et al. | 568/916 |

FOREIGN PATENT DOCUMENTS

| | | | |
|---|---|---|---|
| 231566 | 10/1960 | Australia . | |
| 237492 | 2/1962 | Australia . | |
| 57614 | 10/1966 | Australia . | |
| 12330 | 4/1968 | Australia . | |
| 63512 | 5/1971 | Australia . | |
| 37711 | 7/1973 | Australia . | |
| 68004 | 10/1975 | Australia . | |
| 69538 | 4/1981 | Australia . | |
| 66070 | 5/1981 | Australia . | |
| 5647 | of 1890 | United Kingdom | 568/919 |
| 309708 | 4/1929 | United Kingdom | 568/919 |
| 2060688 | 5/1981 | United Kingdom | 435/161 |

OTHER PUBLICATIONS

Vogel, Arthur "The Textbook of Practical Organic Chemistry" pp. 139–144.
Sherwood, F. "Inorganic & Theoritical Chemistry" p. 287.
Glasstone, S. "Textbook of Physical Chemistry", 2nd edition 1948) p. 729.
Interscience "Guide to the Analysis of Alcohols" pp. A-13 to A-15.
Science "Lowering the Cost of Alcohol" vol. 206, Oct. 5, 1979, pp. 41 and 42.
Process Biochemistry "Energy Conservation in Ethanol Production by Fermentation" Aug. 1983 pp. 31 to 37.
Process Biochemistry "Distillery Effluent Treatment and By-Product Recovery".
SU,A 329161 (Blyum) Jul. 15, 1970 (Derwent English Language Abstract).
SU,A 170941 (Zgekeznyak) Oct. 24, 1964 (Derwent English Language Abstract), Soviet Invention Illustrated Jun. 1966.
SU,A 295747 (Frangul Yan) Jan. 19, 1970 (Derwent English Language Abstract), Soviet Invention Illustrated Nov. 1971.
SU,A 636218 (Shevchuk) Dec. 5, 1978 (Derwent English Language Abstract), E17 67474 B/37.

Primary Examiner—J. E. Evans
Attorney, Agent, or Firm—Murray and Whisenhunt

[57] ABSTRACT

A process for the separation of weak organic acids such as ethanol or methanol from dilute aqueous solutions thereof. The process comprises dissolving in the solution an amount of at least 26 grams/100 ml of solution of a base or a basic salt, such as potassium carbonate, the conjugate acid of which has a pKa value of above 6 and which has a solubility of at least 26 grams/100 ml. of solution and is substantially more soluble in water than in the organic acid, and separating from the solution a phase rich in the organic acid and an aqueous phase rich in the base or basic salt. The process is particularly applicable to the separation of ethanol from fermentation media as the high ionic strength of the dissolved base or basic salt causes flocculation of the dissolved solids component of dunder.

9 Claims, 1 Drawing Figure

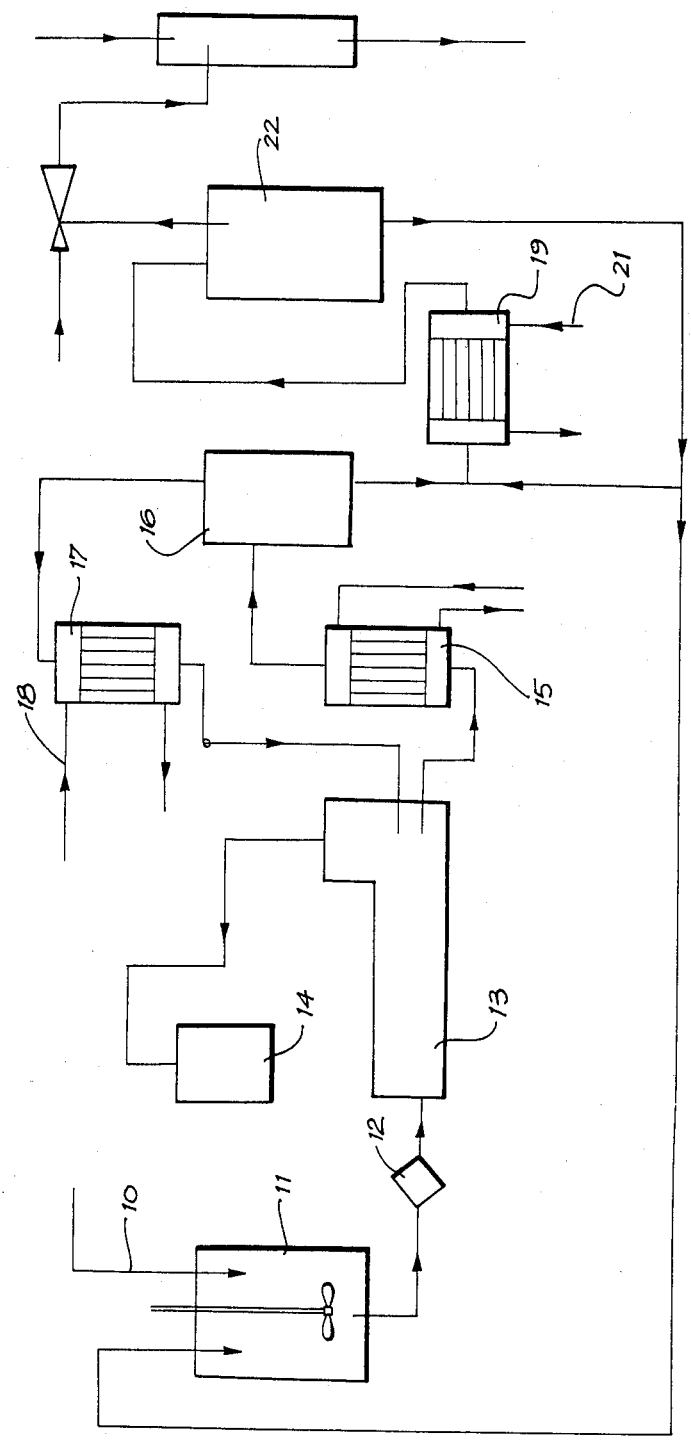

RECOVERY OF ALCOHOLS

The present invention relates to a process for the recovery of weak organic acids such as low molecular weight alcohols from aqueous solutions containing those weak organic acids.

The conventional method for concentrating low molecular weight alcohols (for example methanol and ethanol) from dilute aqueous solutions of these alcohols is by distillation. Using conventional distillation techniques the concentration of, for example, ethanol which can be achieved is 96.5% by volume at which stage an azeotropic mixture of water and ethanol exists. The preparation of anhydrous ethanol requires a further azeotropic distillation with cyclohexane or benzene.

For laboratory preparations and other applications where energy balance considerations are not important, this method has proved satisfactory. However, when ethanol is produced for use as a fuel it is desirable to use as little processing energy as possible so that considerably more energy is obtained in the form of ethanol than is input as heat or electricity. These energy considerations are usually expressed in the form of an energy ratio, defined as the energy available in the ethanol divided by the process energy used to make the ethanol. For production techniques in widespread use at present, this figure varies from 1.5 for a starch raw material to 2.2 for a sugar raw material. These above figures decrease to 1.0 and 1.3 respectively when account is taken of the energy required for the evaporative waste treatment of the effluent from both the fermentation and distillation processes.

Two major criticisms of a fuel ethanol industry are the high processing energy requirement of conventional technology (in particular that of distillation) and the waste disposal problem. Thus two of the key objectives of a process development in the production of ethanol for fuel by fermentation must be to reduce the energy requirements of the process to attain a nett energy balance and to ensure that any waste has virtually no environmental impact.

This invention is, in one aspect, aimed at reducing the energy requirements of the fermentation/distillation process for the production of ethanol. In the conventional process starch or sugar is fermented to ethanol by yeasts or bacteria resulting in a solution of ethanol and other organics in water (usually 8–10% by volume ethanol) which is then concentrated by distillation to 95%–100% v/v ethanol. The invention involves altering the nature of the water component of the alcohol/water mixture such that the aqueous component and the alcohol component are no longer miscible and phase separation occurs. The alcohol phase may then be simply decanted off. It is a further aspect of this invention to induce the flocculation of most of the "dunder" components of a fermented biomass solution. These components may then be simply filtered out as a solid "dry dunder cake".

It has previously been proposed that salts such as potassium carbonate and copper sulphate be used as a dehydrating agent for removing small quantities of water from concentrated alcohol (see "Inorganic and Theoretical Chemistry", F. Sherwood Taylor, P287 and "Guide to the Analysis of Alcohols" published by Interscience, page A-13). It has also been proposed to use potassium carbonate to assist in the partitioning extraction of alcohol from blood. In this case equal amounts of blood and propyl acetate are mixed with potassium carbonate resulting in the alcohol being partitioned with the propyl acetate (see "Guide to the Analysis of Alcohols" published by Interscience, Pages A-14 and A-15). These prior art proposals do not however suggest or disclose that the phase separation of alcohols or other weak organic acids can be induced from dilute solutions by a selected group of base or basic salts of the type to which the present invention relates. Nor does this prior art suggest that the high ionic strength of such bases and basic salts can be used to induce flocculation of the soluble solid component of dunder from fermentation media.

The present invention consists in a process for the separation of a weak organic acid from an aqueous solution containing no more than 40% by volume of that weak organic acid comprising dissolving in the solution an amount of at least 26 grams/100 ml of a base or basic salt the conjugate acid of which has a pKa value of above 6 and which base or basic salt has a solubility in the solution of at least 26 grams/100 ml of solution and is substantially more soluble in water than in the weak organic acid, and separating from the solution a phase rich in the weak organic acid and an aqueous phase rich in the base or basic salt.

As is well known in chemistry the symbol pKa indicates the logarithm of the reciprocal of the dissociation constant of an acid.

The weak organic acids which may be separated from dilute aqueous solutions are those having a pKa of greater than 14. The preferred weak organic acids are the low molecular weight alcohols which have an appreciable solubility in water. The most common of these low molecular weight alcohols are methanol and ethanol.

The preferred basic salts are those which have a conjugate acid which has a pKa of above 7, and the most preferred such salt is anhydrous potassium carbonate which has the advantage of a high solubility in water but is substantially insoluble in the lower alcohols or other weak organic acids. The conjugate acid of potassium carbonate has a pKa value of 10.25. Other bases or basic salts which could be used include sodium carbonate, sodium citrate, potassium hydroxide, sodium hydroxide, rubidium carbonate and cesium carbonate.

The phase separation is preferably induced by dissolving the base or basic salt in the water/alcohol mixture until the solution is substantially saturated with the base or basic salt. The best concentration of the base or basic salt may be determined by simple experimentation however in practice it has been found that concentrations of at least 26 grams/100 ml are required and of at least 100 grams/100 ml are preferred. The higher the concentration of the base or basic salt in the solution the less hydrated will be the separated organic phase. Thus the addition of 26 grams of sodium carbonate per 100 ml of an alcohol/water solution induces the separation of an alcohol phase containing from 60 to 70% v/v alcohol whereas 100 grams of sodium carbonate per 100 ml of solution induces the separation of an alcohol phase containing from 80 to 90% v/v alcohol.

The base or basic salt preferably is not substantially soluble in the organic acid and therefore it dissolves only in the water component of the mixture. In the case of carbonate salts, since both water and bicarbonate ion are considerably stronger acids than aliphatic alcohols the relevant equilibria are:

$$CO_3^{2-} + H_2O \rightleftharpoons HCO_3^- + OH^- \tag{1}$$

$$ROH + OH^- \rightleftharpoons RO^- + H_2O \quad (2)$$

no reaction where ROH = aliphatic alcohols.

Phase separation of the alcohol and aqueous components occurs because the hydrogen-bonding/protonation mechanism of alcohol/water miscibility, viz:

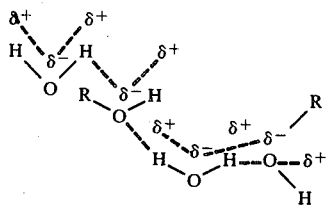

is destroyed, due to the high concentration of hydroxyl ion. The bicarbonate ion is a stronger acid than ROH hence the reverse of reaction (1) applies and not reaction (2).

The base used to induce the phase separation can be an hydroxyl ion, but hydroxyl salts are not preferred because of their high solubility in low molecular weight alcohols. The solubility of the basic compound used to induce the phase separation is an important consideration as sufficient must be dissolved to considerably reduce the effective concentration of water by interaction of the water with the base. For basic salts other than hydroxide the higher the pKa value of the conjugate acid the lower the effective concentration of water.

EXAMPLE 1

An example of the phase separation induced is as follows:

To an initial mixture containing 360 mls of water and 40 ml of ethanol, 440 grams of anhydrous potassium carbonate were added and the mixture stirred until all of the potassium carbonate had dissolved:

|  | Ethanol | Water | Potassium Carbonate |
|---|---|---|---|
| Top layer | ~40 mls | ~3% v/v | — |
| Bottom layer | ~0.5 v/v | ~360 mls | 440 grams |

The amount of alcohol remaining in the aqueous potassium carbonate phase represents the solubility of alcohol in that aqueous medium. This figure is lower for higher concentrations of potassium carbonate. Because the vapour pressure of the alcohol remaining in the potassium carbonate solution is higher than that of a solution of alcohol and water alone the amount of energy required to recover this remaining alcohol is small.

EXAMPLE 2

Tables 1A and 1B list further examples which illustrate that the induced phase separation is dependent upon the pKa value of the conjugate acid of the basic compound used, and is independent of the ionic strength of the basic compound/water/alcohol solution.

TABLE 1A

PHYSICAL CONSTANTS OF BASE OR BASIC SALTS

| Compound | Solubility grams/100 ml Water Cold | Water Hot (at temperature indicated in °C.) | Ethanol | Molecular Weight | pKa conjugate acid |
|---|---|---|---|---|---|
| Potassium Iodide (KI) | 127.5(0°) | 208 (100°) | 1.88(25°) | 166.01 | 0.77 |
| Potassium Thiocyanate (KNCS) | 177.2(0°) | 217 (20°) | soluble | 97.18 | 0.85 |
| Potassium Acetate (KC₂H₃O₂) | 253(20°) | 492 (62°) | 33 | 98.15 | 4.75 |
| Potassium Citrate (K₃C₆H₅O₇.H₂O) | 167(15°) | 199.7 (31°) | slightly soluble | 324.42 | 6.39 |
| Potassium Carbonate (K₂CO₃) | 112(20°) | 156 (100°) | insoluble | 138.21 | 10.25 |
| Potassium Hydroxide (KOH) | 107(15°) | 178 (100°) | very soluble | 56.11 | >14 |

TABLE 1B

PHYSICAL CONSTANTS OF SOLUTIONS OF BASE OR BASIC SALTS/WATER/ALCOHOL

| Compound | 10% v/v aqueous solution of alcohol to which compound is added — Molar concentration of compound | Ionic strength of resultant solution | Volume of separated alcohol phase as (approx) percentage of volume of alcohol in original aqueous solution |
|---|---|---|---|
| Potassium Iodide (KI) | 10.00 | 10.00 | 0 |
| Potassium Thiocyanate (KNCS) | 22.64 | 22.64 | 0 |
| Potassium Acetate (KC₂H₃O₂) | 22.42 | 22.42 | 0 |
| Potassium Citrate (K₃C₆H₅O₇.H₂O) | 5.24 | 31.44 | <10 |
| Potassium Carbonate (K₂CO₃) | 7.96 | 23.88 | 100 |
| Potassium Hydroxide (KOH) | 21.39 | 21.39 | 100 |

Hereinafter described is an integrated ethanol-water separation/fermentation effluent waste treatment process utilising the process according to the present invention.

A pilot plant for the continuous recovery of ethanol from aqueous solution, were designed and built from the concept that had initially been developed in the laboratory. The process is depicted diagramatically in the drawing annexed hereto. A synthetic hydrated ethanol solution was prepared using 95% v/v ethanol (industrial methylated spirit also called I.M.S.) and water. This solution did not contain any yeasts, other organics or impurities which would normally be present in fermented organic solutions or in fermented biomass.

Referring to the attached drawing, the prepared feed solution is fed through inlet line 10 and mixed with potassium carbonate ($K_2CO_3$) in mixing tank 11 until an approximately 50% w/v carbonate solution is obtained. The mixed solution is pumped from tank 11 through filter 12 to a separation tank 13 at the rate of approx. six (6) liters/min. The ethanol, having a lower specific gravity than the potassium carbonate solution, is decanted into a holding tank 14. The underflow from separation tank 13 passes through a heat exchanger 15 at a pressure of 25 P.S.I. and is heated to 93° C. Any remaining alcohol vaporises in flashing tank 16. The alcohol vapour from the flashing tank 16 is condensed in condenser 17, cooled by cooling water flowing through line 18 and returned to the separation tank 13.

The potassium carbonate solution which remains in flashing tank 16 is pumped through heat exchanger 19, heated by steam admitted through line 21, to a subatmospheric single stage evaporator 22 operating at a pressure of 2-4 P.S.I. absolute. Recirculation through heat exchanger 19 allows the solution to achieve 67% concentration, which is still a pumpable slurry. This concentrated slurry is then pumped back to mixing tank 11 for dilution with fresh feed before being recirculated.

Examples from two non-consecutive runs are given below.

EXAMPLE 3

An 880 liter batch of hydrated ethanol and potassium carbonate was prepared in mixing tank 11. The proportioning of the ingredients was as follows:

| | |
|---|---|
| Potassium Carbonate | 48.91% w/v |
| Ethanol | 9.975% v/v |

Five hundred (500) liters was run through the recovery plant at the rate of 6.25 liters/min and the following quantities of ethanol were recovered.

Note: The flash tank 16 was operated cold and used as a separation tank.

| | |
|---|---|
| Quantity of "alcohol" in 14 = | 49.4 liters |
| Quantity of "alcohol" in 16 = | 1.437 liters |
| Total quantity of "alcohol" collected = | 50.837 liters |

The concentration of alcohol recovered was 93.6% v/v corresponding to an equivalent "100% alcohol" content of $$= (50.837)(0.936)$$
$$= 47.58 \text{ liters}$$

The initial alcohol content in 500 liters $$= (500)(9.975)$$
$$= 49.875 \text{ liters}$$

Therefore the alcohol recovery was $$(47.58/49.875)(100) = 95.4\%$$

EXAMPLE 4

73.4 liters of 93.6% (68.7 liters of 100%) ethanol was added to the contents of mixing tank 11 which increased the volume to 807 liters which is equivalent to 8.5% ethanol v/v.

The total amount of alcohol recovered from a throughput of 513.8 liters at an average flow rate of 5.7 liters per minute was:

| | |
|---|---|
| Separation tank 14 yield 96.2% alcohol = | 42.1 liters |
| Flashing tank 16 yield 96.2% alcohol = | 3.17 liters |
| Total 96.2% alcohol = | 45.27 liters | which is equivalent to 43.45 liters of 100% alchol.

| |
|---|
| Percentage of 100% alcohol in 513.8 liters = 8.457% |

Therefore, the alcohol recovery was, $$= \frac{(8.457)}{(8.5)} (100)$$

$$= 99.5\%$$

Currently there is world-wide interest in the development of alternative methods to distillation for the recovery of ethanol for fuel from fermented biomass. Methods under investigation include membrane filtration and gel filtration techniques as well as solvent extraction. It is also widely acknowledged that waste treatment of the effluent from the fermentation (and distillation) process for fuel ethanol production is also a vital consideration, and any attempts to integrate the two processes command great interest.

The major waste from a distillery is the effluent from the first or stripping column. It is known as dunder, stillage, slops, vinasse or vinhoto. The composition depends on sub-substrate to some extent and some figures are given below

TABLE 2
DISTILLARY WASTE COMPOSITION

| | Cassava | Molasses | Cane Juice |
|---|---|---|---|
| pH | 4.8 | 3.7-5.9 | |
| S.G. | 1.05 | | |
| BOD mg/L | 45,000 | 20,000 | |
| COD mg/L | 113,000 | | |
| Dissolved solids % | 10 | | |
| Suspended Solids % | 1 | | |
| Total Solids | 11 | 6-11 | |
| Ash % | 3 | 2-3 | |
| Organic Matter % | 8 | 4.6-8 | 2.9 |

Data on dunder from molasses are more readily available than data from other substrates. Molasses dunder is a rich-brown to black colour with a pleasant smell. There is little precise knowledge of the composition. It contains the non-fermentable substances of the substrate, yeast metabolites and yeast cell contents. These include gums and many substances of plant origin.

Disposable of dunder is a real problem. A 50,000 Kl/annum molasses distillery produces an effluent with a B.O.D. equivalent to the domestic sewage from a city of 1 million people. If fuel ethanol is to become widely used there needs to be a satisfactory solution to waste disposal.

The disposal options possible are:

(i) Discharge to Streams
(ii) Discharge to Sewer
(iii) Discharge to the Ocean
(iv) Aerobic Digestion
(v) Anaerobic Digestion
(vi) Submerged Combustion
(vii) Evaporation and Incineration
(viii) Ultrafiltration
(ix) Stock Feed
(x) Raw material for Single Cell Protein Usage
(xi) Fertiliser Of these the most convenient and environmentally sound approach is to concentrate the dunder to 60% v/v solids by evaporation, and then combust it directly in a special incinerator. The heat of combustion can be used for the evaporation and the ash from the incineration process is a convenient fertiliser, typically 30 to 40% potash ($K_2O$) and 2 to 3% $P_2O_5$.

Evaporation of the dunder, combined with normal distillation, requires about 6 tonnes of steam per kiloliter of ethanol. About 3 tonnes of this can be provided by combusting the dunder solids leaving 3 tonnes to be raised in the normal manner.

It is important that the separation technique utilised is applicable to "real" solutions of fermented biomass. This part of the invention takes the ethanol-water separation process outlined above and applies it to fermented solutions of the type found in practice.

In this aspect the present invention consists in a process for the recovery of a low molecular weight alcohol from an aqueous fermentation medium containing no more than 40% by volume of the alcohol, removing solid particulates (if any) from the fermentation medium, dissolving in the fermentation medium at least 26 gram/100 ml of fermentation medium of base or basic salt the conjugate acid of which has a pKa of above 6 and which salt has a solubility in the solution of at least 26 grams/100 ml of solution and is substantially more soluble in water than in the alcohol to form an alcohol rich phase, and an alcohol poor, salt rich, phase, removing the flocculated particles formed in the fermentation medium after the addition of the base or salt, recovering the alcohol rich phase, and recovering the salt from the salt rich phase in a form suitable for re-use in the present process.

Another aspect of the process according to the present invention is that the high ionic strength created by the addition of the base or basic salt causes most of the soluble dunder components to flocculate. They can then easily be removed as solid "dunder cake" by filtration or centrifugation. Losses of the base or basic salt by this technique are minimal and directly proportional to the moisture content of the separated dunder cake as there appears to be no complexing of such bases or salts with the dunder components.

EXAMPLE 5

"Dead Wash" (the product formed by and resulting from the complete fermentation of molasses—a rich dark brown to black coloured liquid) was obtained from an alcohol distillery and contained approximately 10% dissolved solids, 1% suspended solids and 8% v/v ethanol. To recover the ethanol from the Dead Wash the suspended solids were first removed by filtration. The filtered Dead Wash was then mixed in a mixing tank with anhydrous potassium carbonate in the ratio of 115 grams of potassium carbonate to 100 ml of Dead Wash. Upon mixing the two together the dissolved solids flocculated. In excess of 99% of the flocculated solids were then removed by filtration, in the form of a dry dunder cake.

The separated ethanol phase was light brown in colour as it contained colourants and fusel oils representing weak organic acids with a pKa 14 which were separated along with the ethanol. The concentration of the separated ethanol phase was approximately 97% v/v ethanol.

I claim:

1. A process for the recovery of a low molecular weight alcohol from an aqueous fermentation medium containing no more than 40% by volume of the alcohol, said process comprising:
    dissolving in the fermentation medium at least 26 grams/100 ml of fermentation medium of a base or basic salt the conjugate acid of which has a pKa of above 6 and which salt has a solubility of at least 26 grams/100 ml of fermentation medium and is substantially more soluble in water than in the alcohol, to form (a) an alcohol rich phase; (b) an alcohol poor salt rich phase; and (c) a solid phase of flocculated particles originally dissolved in the fermentation medium;
    recovering the alcohol rich phase and the solid phase separately; and
    recovering the salt from the salt rich phase in a form suitable for reuse in the present process.

2. A process as claimed in claim 1, in which the recovered solid phase is burned to yield heat which is used to evaporate water from the salt rich phase to bring about the recovery of the salt.

3. A process as claimed in claim 1, in which the alcohol is ethanol.

4. A process as claimed in claim 1, in which the base or basic salt is selected from the group comprising potassium carbonate, sodium carbonate, sodium citrate, sodium hydroxide, potassium hydroxide and mixtures thereof.

5. A process as claimed in claim 1, in which the conjugate acid of the base or basic salt has a pKa of above 7.

6. A process as claimed in claim 1, in which the basic salt is potassium carbonate.

7. A process as claimed in claim 1, in which the fermentation medium is substantially saturated with the base or basic salt.

8. A process as claimed in claim 1, in which the salt is recovered as a slurry for reuse in the present process.

9. A process as claimed in claim 1, in which solid particulate matter present in the fermentation medium prior to the addition of the base or basic salt thereto is removed therefrom by filtration prior to such addition of base or basic salt.

* * * * *